(12) United States Patent
Jennissen

(10) Patent No.: US 10,022,227 B2
(45) Date of Patent: Jul. 17, 2018

(54) SUBSTRATE WITH A STRUCTURED SURFACE AND METHODS FOR THE PRODUCTION THEREOF, AND METHODS FOR DETERMINING THE WETTING PROPERTIES THEREOF

(71) Applicant: Herbert Jennissen, Cologne (DE)

(72) Inventor: Herbert Jennissen, Cologne (DE)

( * ) Notice: Subject to any disclaimer, the term of this patent is extended or adjusted under 35 U.S.C. 154(b) by 131 days.

(21) Appl. No.: 14/364,312

(22) PCT Filed: Dec. 16, 2012

(86) PCT No.: PCT/DE2012/100382
§ 371 (c)(1),
(2) Date: Jun. 11, 2014

(87) PCT Pub. No.: WO2013/087073
PCT Pub. Date: Jun. 20, 2013

(65) Prior Publication Data
US 2014/0343687 A1 Nov. 20, 2014

(30) Foreign Application Priority Data
Dec. 16, 2011 (DE) ......................... 10 2011 056 549

(51) Int. Cl.
*A61F 2/26* (2006.01)
*A61F 2/28* (2006.01)
(Continued)

(52) U.S. Cl.
CPC ............. *A61F 2/28* (2013.01); *A61L 17/145* (2013.01); *A61L 27/04* (2013.01); *A61L 27/50* (2013.01);
(Continued)

(58) Field of Classification Search
None
See application file for complete search history.

(56) References Cited

U.S. PATENT DOCUMENTS

2004/0153154 A1* 8/2004 Dinkelacker ........ A61C 8/0012
623/16.11
2005/0049716 A1* 3/2005 Wagener ............. A61F 2/30767
623/23.5
(Continued)

FOREIGN PATENT DOCUMENTS

DE   102009057444 A1   6/2011
EP   1 254 673 A1   11/2002
(Continued)

OTHER PUBLICATIONS

Jennissen, H.P., "Ultra-Hydrophilic Transition Metals as Histophilic Biomaterials", Macromol. Symp., 2005, pp. 43-69, vol. 225.
(Continued)

*Primary Examiner* — Thomas J Sweet
*Assistant Examiner* — Megan Wolf
(74) *Attorney, Agent, or Firm* — Cahn & Samuels, LLP

(57) ABSTRACT

An implant includes a microstructured hyperhydrophilic surface with protrusions and depressions in which a spacing between the protrusions as a statistical mean is in a range of 1 to 100 μm and a profile height of the protrusions and depressions as a statistical mean is in the range of 1 to 80 μm.

11 Claims, 16 Drawing Sheets

(51) Int. Cl.
*A61L 27/50* (2006.01)
*A61L 17/14* (2006.01)
*A61L 27/04* (2006.01)
*B23K 26/00* (2014.01)
*C23C 4/08* (2016.01)
*C23C 4/18* (2006.01)
*C23C 4/134* (2016.01)
*G01N 13/02* (2006.01)

(52) U.S. Cl.
CPC ............ *B23K 26/0066* (2013.01); *C23C 4/08* (2013.01); *C23C 4/134* (2016.01); *C23C 4/18* (2013.01); *G01N 13/02* (2013.01); *A61F 2002/2835* (2013.01); *A61F 2310/00011* (2013.01); *A61L 2400/18* (2013.01); *G01N 2013/0283* (2013.01); *G01N 2013/0291* (2013.01)

(56) References Cited

U.S. PATENT DOCUMENTS

| | | | |
|---|---|---|---|
| 2005/0119758 A1* | 6/2005 | Alexander | A61F 2/30771 623/23.5 |
| 2006/0147332 A1 | 7/2006 | Jones et al. | |
| 2007/0005024 A1 | 1/2007 | Weber et al. | |
| 2008/0195216 A1 | 8/2008 | Philipp | |
| 2009/0035723 A1* | 2/2009 | Daniel | A61L 27/50 433/215 |
| 2010/0168854 A1 | 7/2010 | Luers et al. | |
| 2010/0218854 A1* | 9/2010 | Garcia Saban | A61L 27/06 148/269 |
| 2010/0226943 A1* | 9/2010 | Brennan | A41D 31/0077 424/400 |
| 2011/0033661 A1 | 2/2011 | Oawa | |
| 2012/0305681 A1 | 12/2012 | Fritz et al. | |
| 2013/0009338 A1* | 1/2013 | Mayer | B29C 67/0055 264/241 |

FOREIGN PATENT DOCUMENTS

| | | |
|---|---|---|
| EP | 1 683 593 A2 | 7/2006 |
| EP | 2121058 A2 | 11/2009 |
| WO | 2003073045 A1 | 9/2003 |
| WO | 2006135755 A2 | 12/2006 |

OTHER PUBLICATIONS

International app. No. PCT/DE2012/100382, "International Preliminary Report on Patentability", dated Jun. 2014.
English Abstract of WO 2003073045.
Ennissen, et al., "Biocoating of Implants with Mediator Molecules: Surface Enhancement of Metals by Treatment with Chromosulfuric Acid", Mat.-wiss. u. Werkstofftech, 30, 838-845 (1999).

* cited by examiner

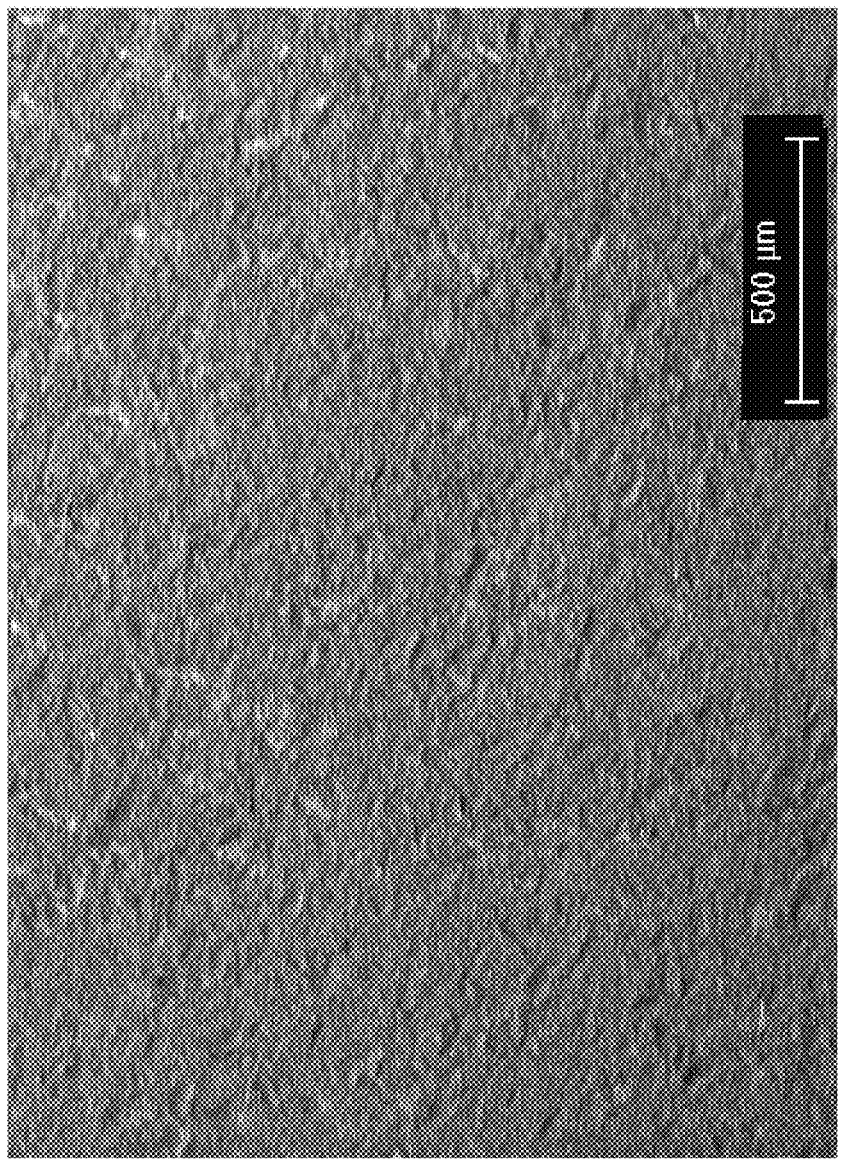
Fig. 1 - A. SLA-surface 50 x
PRIOR ART

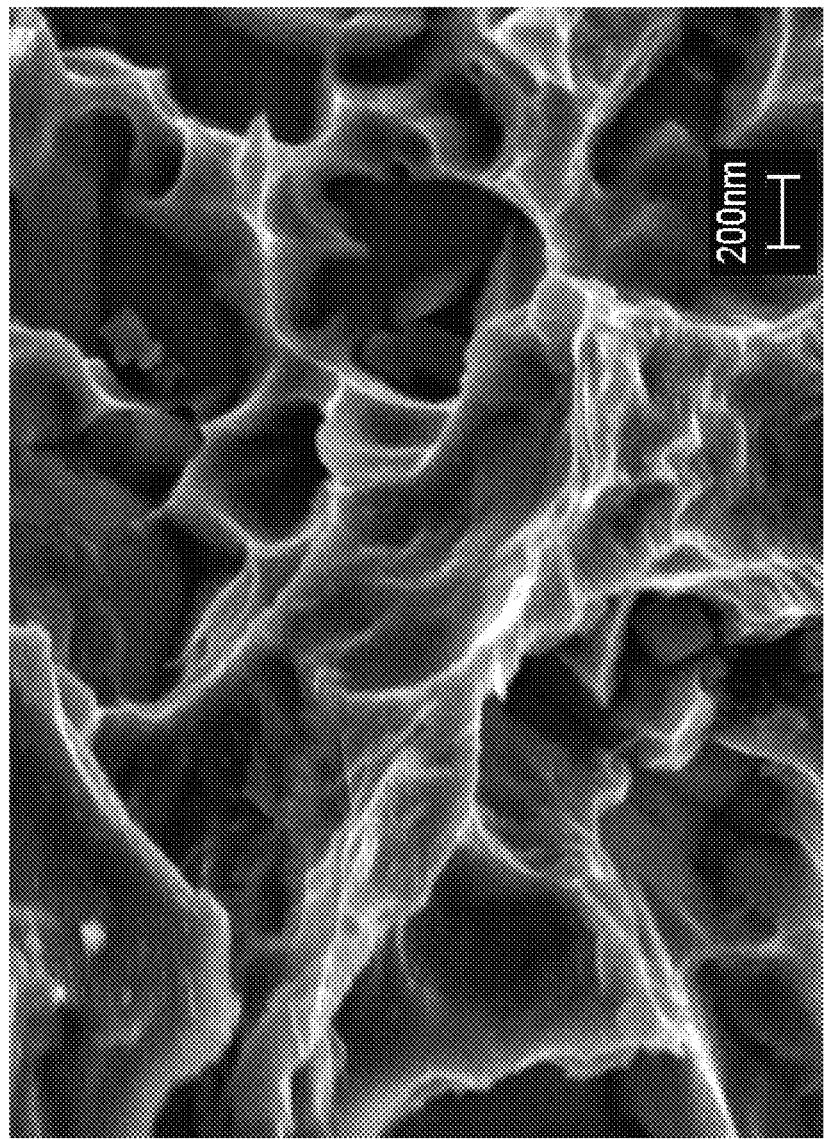
Fig. 1 - B. SLA-surface 25 000 x
PRIOR ART

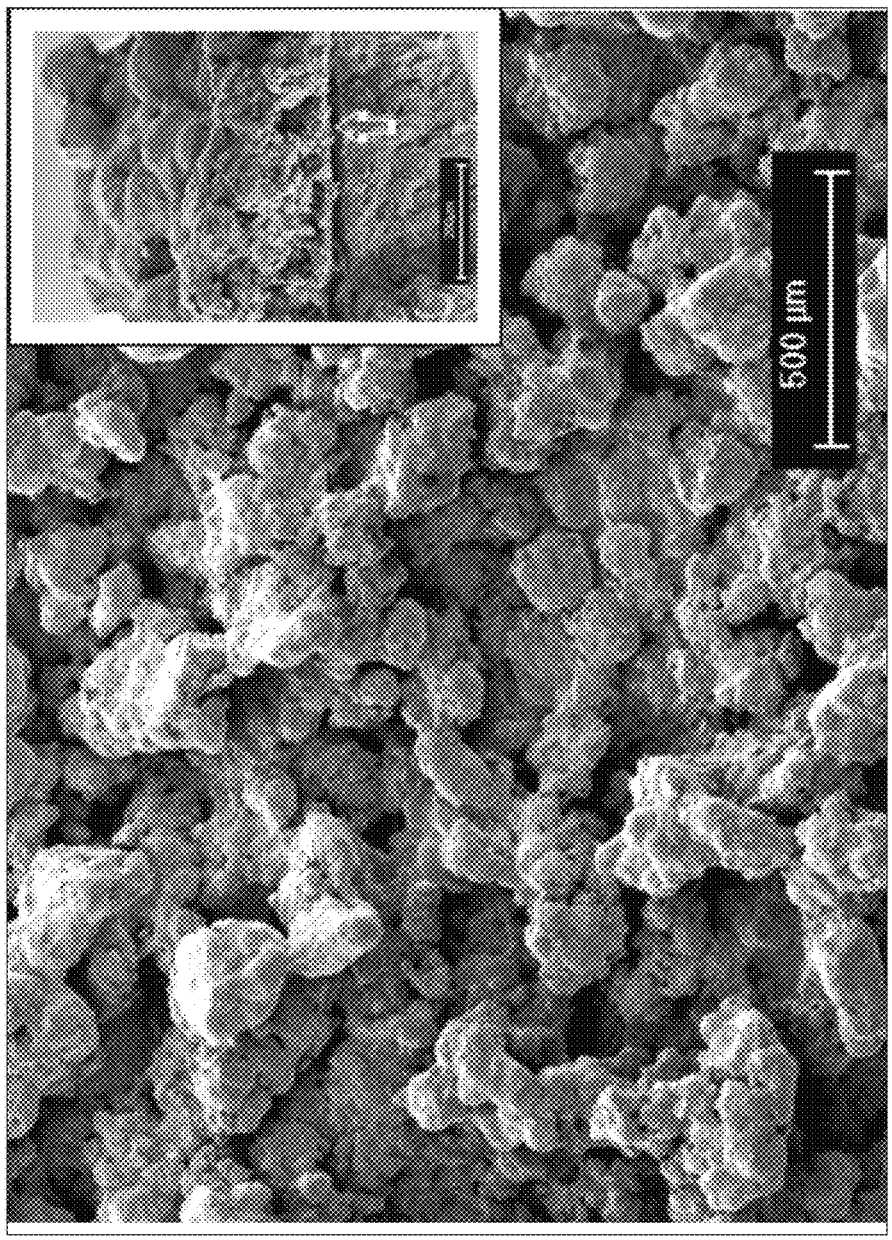
Fig. 1 - C. TPS- surface 50 x
PRIOR ART

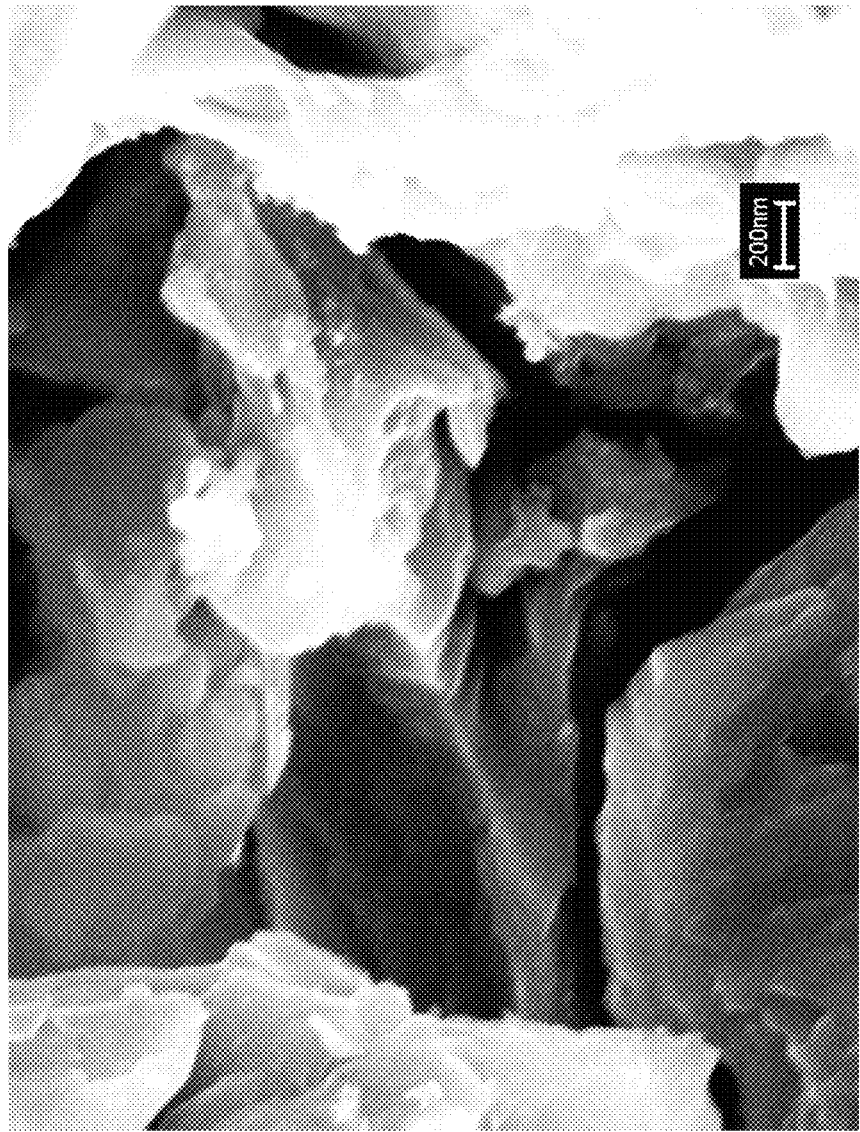
Fig. 1 - D. TPS- surface 25 000 x
PRIOR ART

Fig. 2 - A. Sinusoidal profile (Ra = 50 µm, λ = 32 µm)
General basic function: $A_R(x) = (\sin(x))$
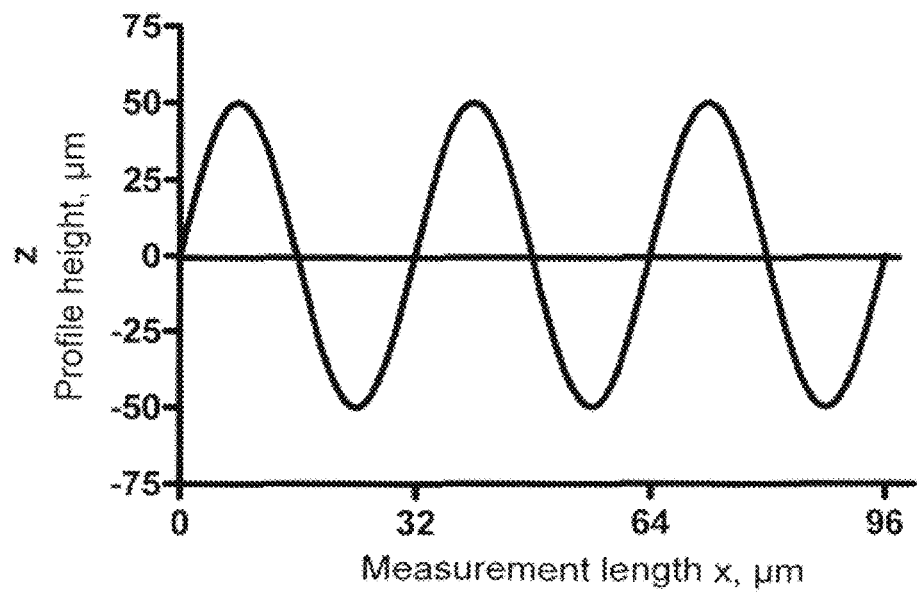
Defined profile function: $z = A_R(x) = (\sin(\frac{2\pi}{32}x))50$

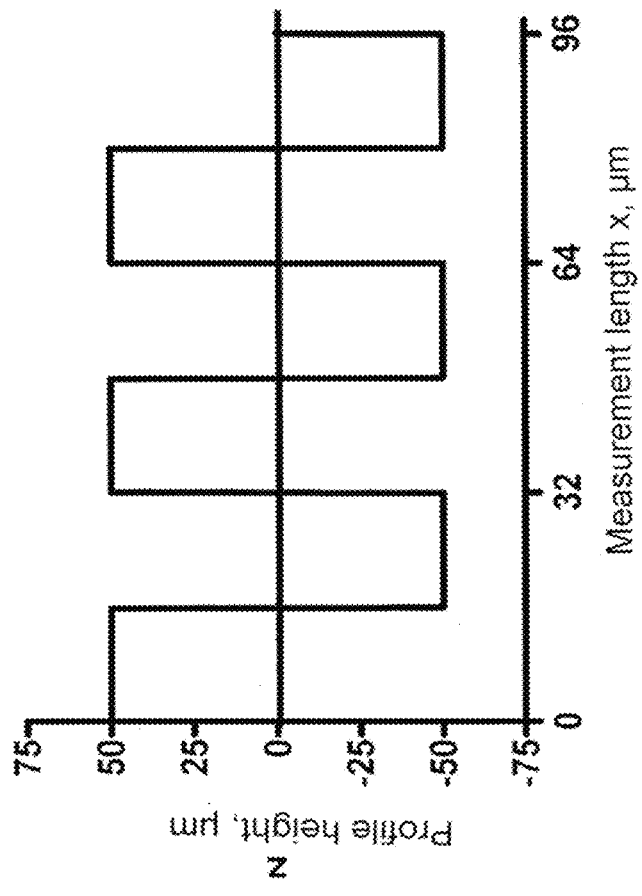
Fig. 2 - B. Rectangular profile (Ra = 50 μm, λ = 32 μm)
$$A_R(x) = \frac{4a}{\pi}\left(\sin(x) + \frac{1}{3}\sin[3x] + \frac{1}{5}\sin(5x) + \frac{1}{7}\sin(7x) + \frac{1}{9}\sin(9x) + \ldots\right)$$

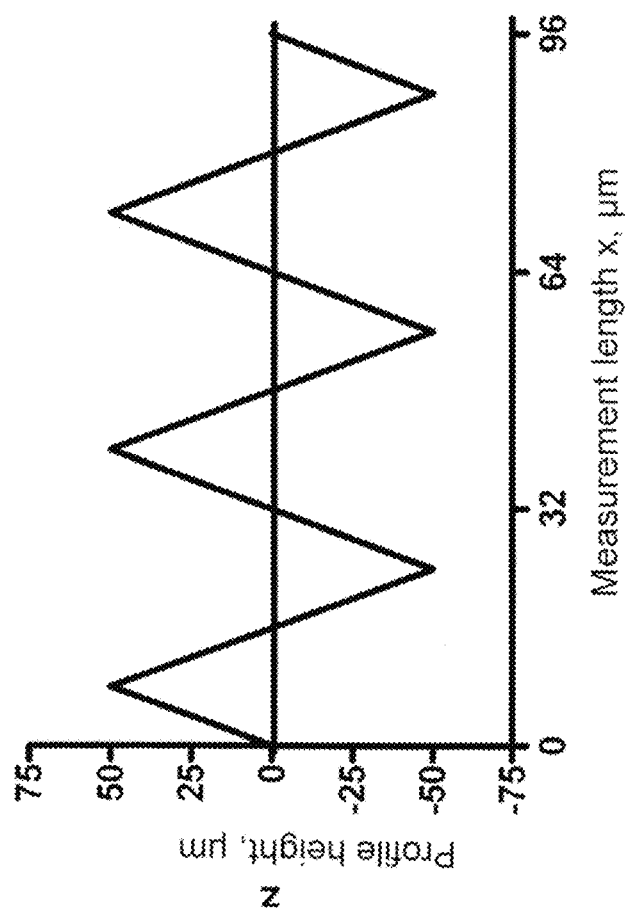
Fig. 2 - C. Triangular profile (Ra = 50 μm, λ = 32 μm)
$$A_R(x) = \frac{4a}{\pi}\left(\sin(x) - \left(\frac{1}{3}\right)^2 \sin(3x) + \left(\frac{1}{5}\right)^2 \sin(5x) - \left(\frac{1}{7}\right)^2 \sin(7x) + \left(\frac{1}{9}\right)^2 \sin(9x) + \ldots\right)$$

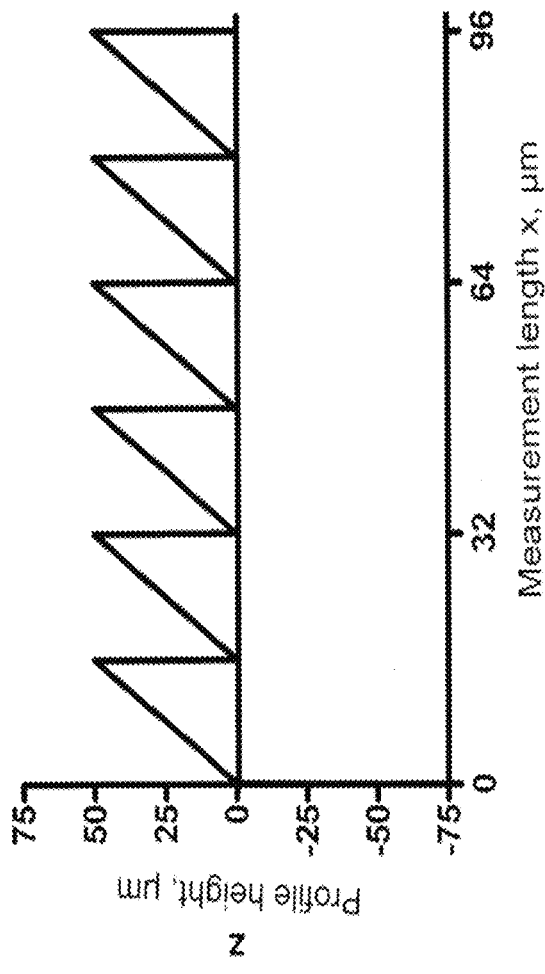
Fig. 2 - D. Sawtooth profile (Ra = 25 μm, λ = 32 μm)
$$A_R(x) = \frac{2a}{\pi}\left(\sin(x) - \frac{1}{2}\sin(2x) + \frac{1}{3}\sin(3x) - \frac{1}{4}\sin(4x) + \frac{1}{5}\sin(5x) + \ldots\right)$$

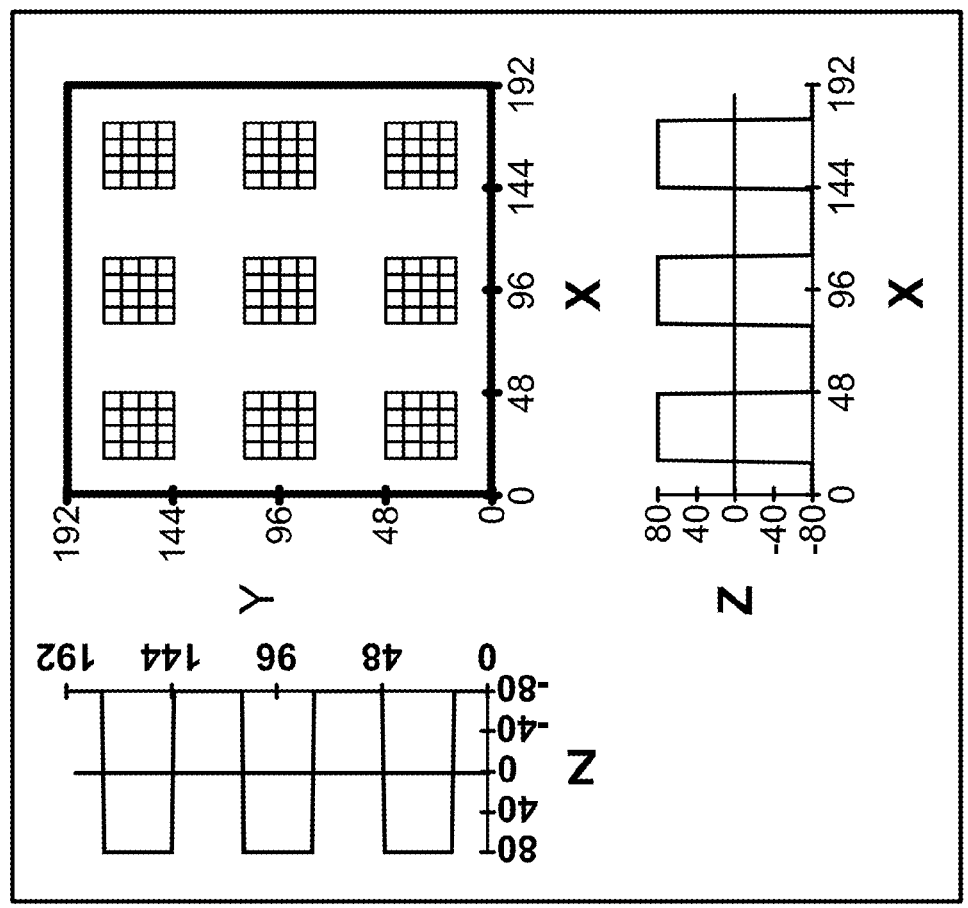
Fig. 3 - A.

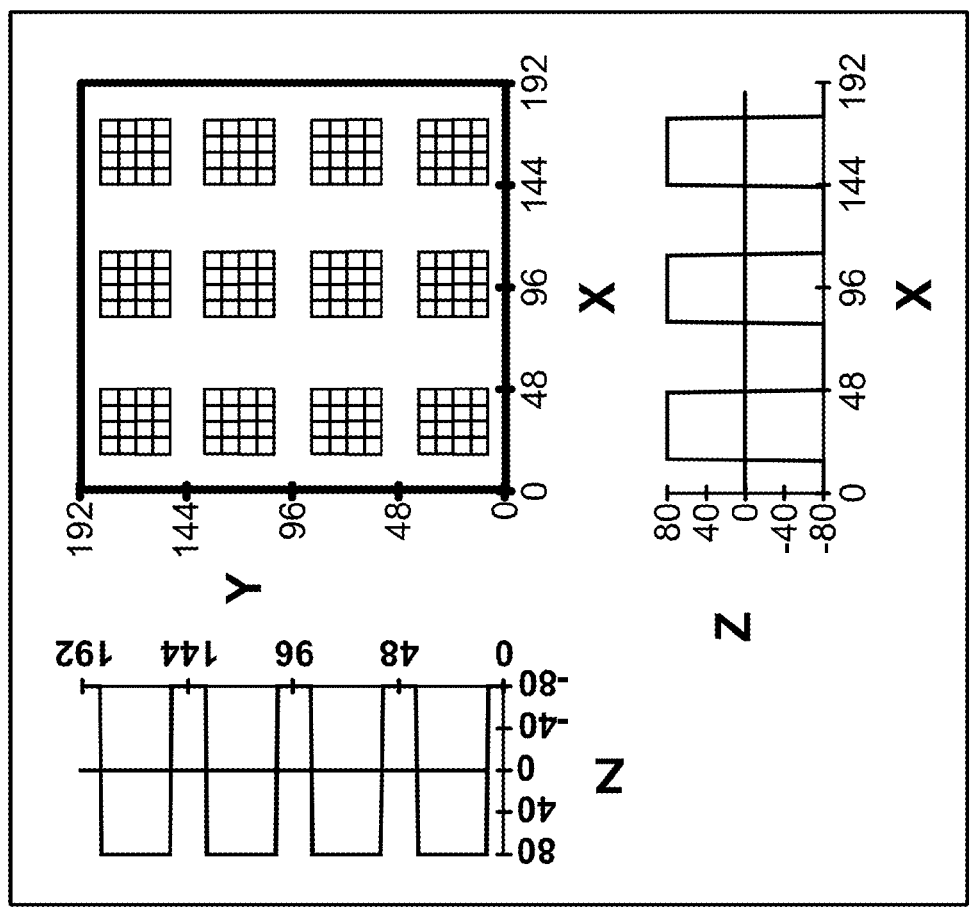

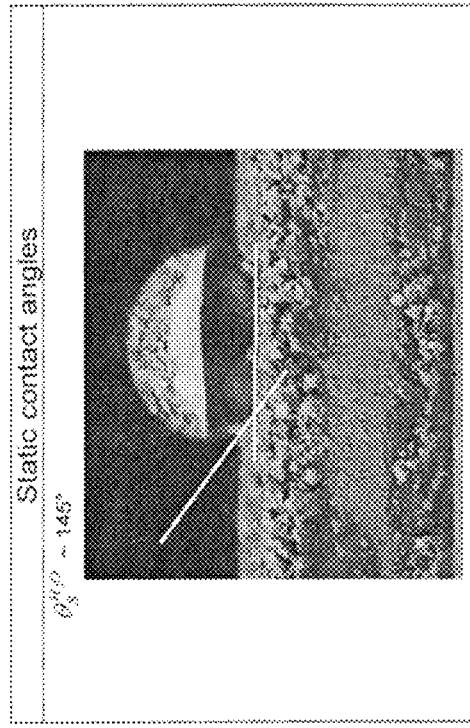
Fig. 5 – A
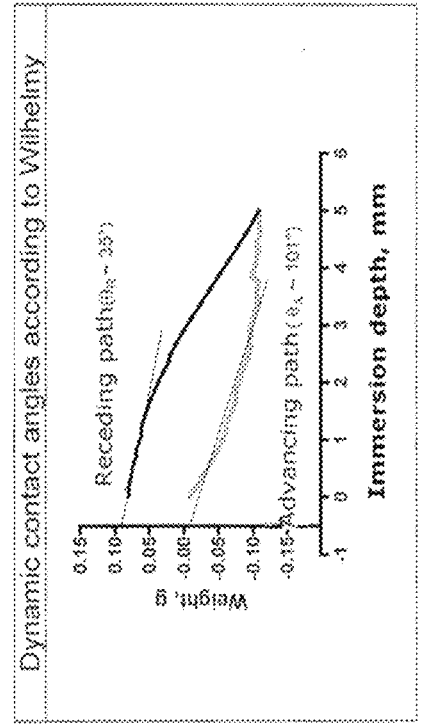
Fig. 5 – B

SUBSTRATE WITH A STRUCTURED SURFACE AND METHODS FOR THE PRODUCTION THEREOF, AND METHODS FOR DETERMINING THE WETTING PROPERTIES THEREOF This U.S. patent application is a national stage application of PCT/DE2012/100382 filed on 16 Dec. 2012 and claims priority of German patent document DE 10 2011 056 549.3 filed on 16 Dec. 2011, the entireties of which are incorporated herein by reference.

BACKGROUND OF THE INVENTION

The invention concerns a substrate with a structured surface and methods for the production of the substrate with a structured surface and also methods for determining the wetting properties of that substrate. The method according to the invention can be used to produce in particular substrates with user-specific fixed surface properties—implants are named by way of example—. Thus implants like for example dental implants or endoprostheses which are distinguished by particularly good ingrowth at the implantation location in the jaw or extremity bones can thus be produced with the method according to the invention.

In recent years it has become increasingly clear that the roughness of the surface of an implant, besides hydrophilicity and hydrophobicity of the implant surface, plays one of the most important parts in the integration of implants. Roughness can increase by hydrophilicity and also hydrophobicity. Thus it is known in the state of the art that an SLA (sand-blasted acid etched) surface exhibits a substantially better ingrowth behaviour than the smooth machined form of titanium. Besides the SLA surface with a roughness there are implants with a TPS (titanium plasma sprayed) surface, which exhibits a roughness with a better integration healing behaviour.

The presence of a rough surface is always linked to an increase in surface area in comparison with a smooth surface. Thus for example the SLA and TPS surfaces, in comparison with a smooth surface, can have a surface area which is 2-20 times greater, and that has a positive effect in particular in the case of ingrowth in animals and humans.

A disadvantage of rough surfaces is the problem of removal in the event of implant revisions. What is common in particular to the previously produced implants is that the outwardly facing surfaces of the object generally have irregular structures which adversely affect the ingrowth behaviour in particular for use of the objects as implants, and do not positively influence same. In addition titanium particles can become detached from the TPS surface and pass into the tissue.

Added to that is a reproduction capability, which needs to be improved, of the implants produced in that way as implants produced both using the SLA method and also using the TPS method exhibit a certain statistical breadth in respect of the surface properties and it is therefore necessary to observe with the utmost accuracy the method parameters in dependence on the starting material for the purposes of standardising the implants.

Consideration was given on the part of the inventor to improving the surface properties and it was discovered that an optimally structured of the implant can be afforded with a microstructure. It was demonstrated by the inventor that reverse engineering leads to a surface with properties which are improved in relation to the two above-mentioned SLA and TPS surfaces, wherein the improved surfaces can be produced with a lower risk potential.

It was further discovered on the part of the inventor that such rough implant surfaces can be made further hyperhydrophilic, as is described hereinafter, by means of wet-chemical methods and/or by functionalisation with hydrophilic organic molecules.

It will be noted however that the production of such hyperhydrophilic surfaces generally requires the use of highly heated acids and the corresponding plasma chambers. In relation to those hyperhydrophilic surfaces hitherto the dynamic contact angles were measured with ultrapure water in the form of the advancing angle ($\theta_V$) and the receding angle ($\theta_R$) in accordance with the observations of the inventor with the value zero ($\theta_V/\theta_R=0°/0°$). In reality the contact angles are in the imaginary range.

SUMMARY OF THE INVENTION

The invention is therefore directed to substrates with a microstructured surface which, if desired, is superimposed by a second smaller microstructure and/or by a nanostructure, as well as methods for the production thereof, which have the desired hyperhydrophilic surface properties.

According to the invention a regular microstructure of that kind can be produced by means of various methods. These include structure-removing methods like also structure-building methods which respectively make use of acting upon the object, or of powder, with energy-rich radiation.

In accordance with the information in Mays (2007) "A new classification of pore sizes. *Studies in Surface Science and Catalysis*, 160, 57-62" in relation to pore sizes structures/roughnesses can be appropriately classified as follows:
Nanostructures: 0.1-100 nm
Microstructures: 0.1-100 μm
Millistructures: 0.1-100 mm In that respect the range 0.1-0.99 can be referred to as "submicrostructure".

According to the invention laser removal can be highly selectively used as the structure-removing method in order to remove individual layers from the substrate without significant damage to the subjacent layers or the substrate. The removed structures can be both in point or line form and also over a surface area.

According to the invention the following are to be named as structure-building or layer-building methods for the production of three-dimensional objects like implants: rapid prototyping, rapid tooling, rapid manufacturing, laser sintering, laser microsintering and EBM.

According to the invention laser microsintering can be used as a further method of producing microstructures. In that respect processing of ceramic powders in high quality is also possible.

A basic prerequisite for the methods is generally that the geometrical data of the product are present three-dimensionally and can be processed as layer data. According to the invention, from the existing CAD data of the component, the data are converted into a data format, for example an STL format, in order to structure the surface of a blank in specifically targeted fashion by means of the above-mentioned methods or to be able to build up the blank in structured form from powder.

The known apparatuses, including for rapid prototyping methods, respectively have such an STL interface serving to provide geometrical information from three-dimensional data models.

Thus the inventor developed a method with which surfaces provided with regular/periodically recurring microstructures can be produced by the surface of the blank being acted upon with energy-rich radiation in one or more patterns, which can be represented from a periodic function converted into an STL data set, wherein either a structure-building method is employed using particulate material like metal powder or ceramic powder, or a structure-removing method is employed. In the case of a structure-building method an amount of powder present on the blank can be acted upon with the energy-rich radiation in one or more steps and the pattern can be produced on the blank.

As a less complicated and expensive alternative in accordance with the invention a structure-removing method can be employed, in which the desired structure is produced by removal of surface material.

BRIEF DESCRIPTION OF THE DRAWINGS

FIGS. 1A-1D show REM images of typically wide-spread and successful rough surfaces in dentistry and orthopaedics with FIG. 1A and FIG. 1B SLA surface (sand-blasted acid etched); FIG. 10 and FIG. 1D TPS surface (titanium plasma spray method) and the insert of FIG. 10: transfer fracture edge of the TPS surface.

FIGS. 2A-2D shows basic shapes of surface protrusions (profiles) as a side view, with FIG. 2A (sinusoidal profile), FIG. 2B (rectangular profile), FIG. 2C (triangular profile), and FIG. 2D (sawtooth profile).

FIGS. 5A-5B show determination of a static (FIG. 5A) and dynamic (FIG. 5B) contact angle on a superhydrophobic unmodified TPS surface with ultrapure water.

DETAILED DESCRIPTION OF THE INVENTION

Figure 3:
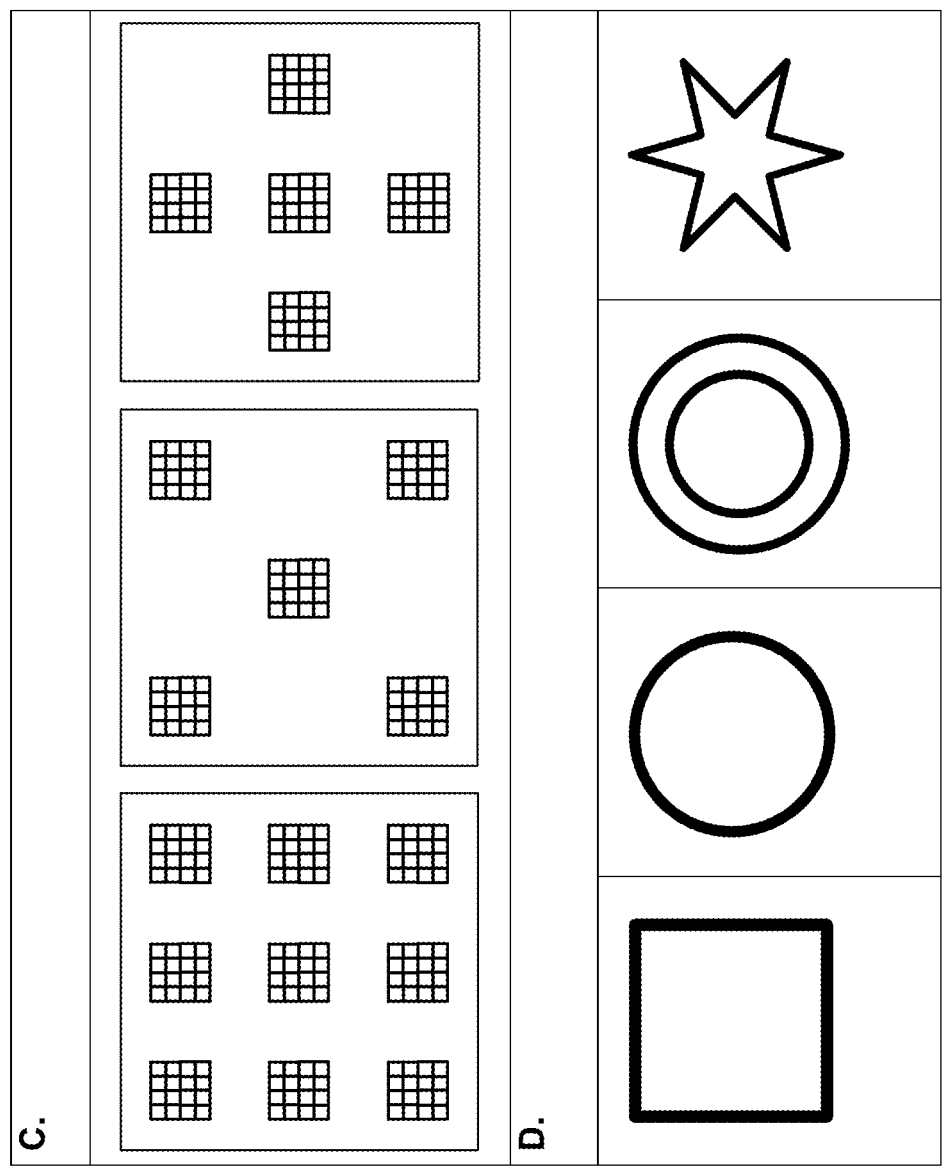
FIGS. 3A-3D show unit cells with the respective associated rectangular functions and some profiles (FIGS. 3A and 3B), arrangement patterns (FIG. 3C) as a cross-sectional view, and hollow cylinders or stellate profiles (FIG. 3D).

More precisely the present invention in an embodiment concerns a method for the production of a substrate with a regularly microstructured surface with protrusions and depressions, wherein the spacing between the protrusions as a statistical mean is in the range of 1.0 to 100 μm and the profile height of the protrusions and depressions as the statistical mean (Ra-value) is in the range of 1 to 80 μm, which comprises the steps:
  a) providing a powder or a powder mixture of a sinterable material powder on a blank;
  b) applying a layer of the metal powder to the surface of the blank; and
  c) acting on the layer of the material powder with energy-rich radiation in a pattern which can be represented from a periodic function converted into an STL data set so that material powder is sintered on at least a partial region of the surface of the blank with the formation of at least a partial region of the pattern.

In the method the blank can be produced from solid material or layer-wise by way of a sintering method from a sinterable material powder.

If required movement or displacement of the blank in the axial or horizontal direction and successive repetition of steps b) to d) can be effected so that a further partial region of the pattern, that adjoins the first partial region of the pattern, can be sintered.

In an embodiment the method includes the successive repetition of steps b) to c) until the surface is completely covered with the desired pattern.

As mentioned above, beside the method of building up a pattern by way of laser sintering or EBM, it is also possible to produce a desired surface microstructure by laser ablation. Thus the invention also concerns a method for the production of a substrate with a microstructured surface, which has the following steps:
  a) providing a blank;
  b) acting on the blank with energy-rich radiation at least partially in a pattern which can be represented from a periodic function converted into an STL data set so that the blank is ablated with the formation of at least a partial region of the pattern on at least a partial region of the surface.

The blank obtained having a regularly microstructured surface by the building-up or removing method can be subjected to a treatment for producing a second regular microstructure using a periodic function converted into an STL data set and/or a wet-chemical treatment for producing a nanostructure.

If required the blank can be moved in the axial or horizontal direction and step b) can possibly be repeated a plurality of times until the substrate surface is provided at least in a partial region with the desired microstructured pattern.

The invention thus also concerns a substrate in which the hyperhydrophilic surface is microstructured irregularly or at least in a partial region regularly.

The material of the blank can be selected from the group of metals, metal alloys, ceramic material (for example zirconium oxide), glasses and polymers (PEEK, polyether ether ketone) and combinations thereof.

In that respect the material of the blank in particular for use as an implant preferably comprises a material selected from the group of metals, metal alloys and combinations thereof with ceramic materials. Preferably the implant material used comprises metallic materials like pure titanium or metallic titanium alloys, chromium/nickel/aluminium/valadium/cobalt alloys (for example TiAlV4, TiAlFe2,5), high-quality steels (for example V2A, V4A, chromium nickel 316L) or a combination thereof with ceramic materials like hydroxylapatite, zirconium oxide, aluminium oxide, in which the metallic is present as a composite material with ceramic material. The non-metallic materials including the polymers like PEEK can however also be used alone without combination with other materials.

According to the invention the microstructured surfaces obtained in that way can be further hydrophilised by a wet-chemical treatment with for example chromo-sulphuric acid, wherein the contact angle when wetting with water can then no longer be measured in accordance with the classic measurement and evaluation procedure or is given as zero, but in accordance with the novel method developed by the inventor can be specified with imaginary numbers.

Such a treatment can be carried out for example in such a way that the surface of the microstructured implant is treated with an oxidising agent insofar as the preferably degreased implant is shock-heated in hot chromo-sulphuric acid—preferably in that respect the chromo-sulphuric acid is of a density of more than 1.40 g/cm$^3$—at a temperature of above 200° C., that is to say it is heated to the temperature of the chromo-sulphuric acid by immersion within a few seconds and is left there at that temperature for a period of 10 to up to 90 minutes, preferably up to 60 minutes, particularly up to 30 minutes, and thereafter directly after removal the implant is cooled down to ambient temperature within a period of less than a minute, preferably within a few seconds. That can preferably be effected by the implant being quenched by immersion in concentrated sulphuric acid at a temperature of 15° C. to 25° C. In order to remove residues of acid and, if present, metal ions which are foreign to the implant, for example chromium ions, the surface of the metal implant is washed in a plurality of washing steps (up to 15) with distilled water. If thereafter chromium ions are still to be detected on the surface of the implant then the implant can be treated with a solution of a complexing agent until no further metal ions can be detected. The inventor surprisingly found that, when using EDTA as the complexing agent the solution is coloured as brown-violet violet when chromium is dissolved out of the samples. The inventors propose accordingly for the situation that the samples are washed in 10% EDTA (1-3×) at pH 7, if required also in boiling EDTA solution, until no further colouration by chromium ions occurs.

Thus, by means of this method according to the invention, it is possible to obtain an implant with a hyperhydrophilic surface, which can be made storable in accordance with a further configuration of a method in accordance with EP 2 121 058.

There the inventors carried out tests which gave surprising results in comparison with the teachings known in the state of the art. Because of the increased cost of wet packagings for preserving hydrophilic and ultrahydrophilic surfaces on implants which, in the case of the ultrahydrophilic metal implants according to the invention, surprisingly permit storage-stable implants without a loss of wettability even at relatively high levels of salt concentration of more than 0.5 M/I, liquid-free packaging methods were also sought. In that respect it was found that hyperhydrophilic surfaces on which salt solutions were left to evaporate also became stable in relation to the loss of wettability. Evaporation can be effected under a protective gas or in atmospheric air, wherein the latter has been used as standard because of the aspect of simplicity.

After evaporation a fine macroscopically invisible "exsiccation layer" was formed on the surface treated in that way, which layer in accordance with the invention stabilises and protects both the ultrahydrophilicity and also hyperhydrophilicity. In general, in accordance with the invention, it is possible to use neutral salt solutions in solution of a single salt or also various salts in a concentration and amount which is inert in relation to the ultrahydrophilic surface and is sufficient to cover the surface of the implant with the exsiccation layer after evaporation. Evaporation can be performed when the implant is in the solution of neutral salt, or when the implant has been removed from the solution and is thus covered only with a thin layer of that solution. A corresponding consideration also applies to the hyperhydrophilic implants described here.

The invention therefore also includes a method which besides the above-described steps for the production of the substrate, includes the additional step that the surface obtained is protected, stabilised and made capable of long-term storage of means of a solution of non-volatile substances like salts, organic solvents which do not interact with the surface, or a salt-bearing exsiccation layer, to protect the surface of the substrate in relation to deterioration due to aging or sterilisation methods (for example gamma sterilisation).

The invention is also directed to a substrate with a microstructured hyperhydrophilic surface with protrusions and depressions, wherein the spacing between the protrusions as a statistical mean is in the range of 1 to 100 µm and the profile height of the protrusions and depressions as a statistical mean (Ra value) is in the range of 1 to 80 µm, wherein at least one of the two dynamic contact angles ($\theta_V$ and $\theta_R$) is in the hyperhydrophilic range with $$\frac{\Delta F}{P \cdot y} > 1.0 \text{ to } 2.15 \ (\theta_{ai} > 0, 0i° - 80i°),$$

in particular with $$\frac{\Delta F}{P \cdot y} > 1.0 \text{ to } 1.0619 \ (\theta_{ai} > 0, 0i° - 20i°).$$

The invention further includes a substrate as defined hereinbefore in which the first microstructure with first protrusions and depressions is superimposed by a second microstructure with second protrusions and depressions, wherein the spacing between the second protrusions as a statistical mean is in the range of 0.1 to 10 µm and the height of the second protrusions and depressions as a statistical mean (Ra value) is in the range of 0.1 to 10 µm.

Preferably the spacing between the second protrusions as a statistical mean is in the range of 0.1 to 5 µm and the height of the second protrusions is in the range of 0.1 to 5 µm.

The microstructure with the first protrusions and depressions or the microstructure with the second protrusions and depressions can be superimposed by a nanostructure which can be produced by a wet-chemical treatment, for example by acid etching, as described hereinafter.

It is advantageous if the surface has a regular first structure and the spacings and heights of the first protrusions are in the above-defined limits. That first microstructure is preferably produced by the surface of the blank being acted upon with energy-rich radiation in a pattern which can be represented from a periodic function converted into an STL data set. That periodic function is preferably a trigonometric basic function $A_R(x)$ which is selected from:

$$A_R(x) = (\sin(x), \tag{1}$$

$$A_R(x) = \frac{4a}{\pi}\left(\sin(x) + \frac{1}{3}\sin[3x] + \frac{1}{5}\sin(5x) + \frac{1}{7}\sin(7x) + \frac{1}{9}\sin(9x) + \ldots\right), \tag{2}$$

$$A_R(x) = \frac{4a}{\pi}\left(\sin(x) - \left(\frac{1}{3}\right)^2\sin(3x) + \left(\frac{1}{5}\right)^2\sin(5x) - \left(\frac{1}{7}\right)^2\sin(7x) + \left(\frac{1}{9}\right)^2\sin(9x) + \ldots\right), \tag{3}$$

$$A_R(x) = \frac{2a}{\pi}\left(\sin(x) - \frac{1}{2}\sin[2x] + \frac{1}{3}\sin(3x) - \frac{1}{4}\sin(4x) + \frac{1}{5}\sin(5x) + \ldots\right), \quad (4)$$

or derivatives thereof.

An optional second microstructure which is superimposed on the first microstructure is preferably produced by the surface of the blank being acted upon with energy-rich radiation in a pattern which can be represented from a periodic function converted into an STL data set. That periodic function can preferably be a trigonometric basic function $A_R(x)$ as specified hereinbefore, which with other variables leads to a lesser "wavelength" and "amplitudes" of the microstructure.

The inventive development on the part of the inventor is based on the realisation that as an important parameter the profilometric arithmetic mean value of the roughness (Ra value) gives information about the topography of the surface.

For that purpose, in accordance with the considerations on the part of the inventor, a reference line is placed on a substrate surface in such a way that the area of the peaks and valleys becomes equal. In that case Ra is defined as the arithmetic mean of the absolute deviations of the profile heights upwardly and downwardly in μm. The following simplified equation describes the Ra value:

$$R_a = (z_1 + z_2 + z_3 + z_n)/n [\mu m] \quad (5)$$

The absolute value of the profile height (positive or negative height on the y-axis) related to the profile reference line is named z. L is a defined measurement length (window) along the x-axis. In idealised terms such a surface profile corresponds to a regular sinusoidal oscillation with the extreme values ±z in deviation from the reference line (zero line) (see FIG. 2A). Besides the Ra value a second topographic parameter is also defined in μm as the maximum profile height Ry (=total of highest profile peak and deepest profile valley). Finally, it is to be noted that surfaces with identical Ra values can have non-identical surface profiles.

A further roughness parameter is the dimensionless microscopic roughness factor $r_m$:

$$r_M = \frac{\text{actual area}}{\text{geometrical area}} = \frac{A'}{A'} \quad (6)$$

wherein A' represents the measured increased surface area in comparison with the calculated geometrical surface area A. The microscopic roughness factor r which is generally captured by means of a laser scanning microscope (LSM) gives information about the microscopic increase in size of the surface area due to the increasing roughness.

In cell cultures it has been found that regular structures without sharp edges on the biomaterial surface of cells are preferred. It has further been found that, in surfaces with narrow-neck pores, as can occur for example in TPS surfaces, biofilms are formed, which can cause implant loosening. The aim therefore is to provide a surface without such pores.

The structuring of the substrates surface in the pattern which can be represented from a periodic function converted into an STL data set imparts to the substrate properties which can be influenced by a variation in given parameters like for example roughness (Ra values), periodicity value, microscopic roughness factor $r_M$, spacing between the protrusions or maximum profile height Ry. According to the invention substrates and methods for the production of substrates are preferred, which have or produce a roughness parameter Ra in the range of 1-250 μm, preferably between 1 and 80 μm and particularly preferably between 2 and 30 μm. According to the invention substrates and methods for the production of substrates are preferred, which have or produce a periodicity value n (λ/2) in the range between 1 and 100 μm, preferably between 10 and 60 μm and particularly preferably between 2-30 μm. According to the invention substrates and methods for the production of substrates are preferred, which have or produce a microscopic roughness factor $r_M$ in the range between 2 and 50. According to the invention substrates and methods for the production of substrates are preferred, which have or produce a spacing between the protrusions as a statistical mean in the range of 1 to 100 μm. According to the invention substrates and methods for the production of substrates are preferred, which have or produce a maximum profile height Ry in a range of 2 to 500 μm.

The inventor developed the idea for the production of implants with a homogeneous and defined roughness by way of consideration of the roughness as a sine curve. That is shown in FIG. 2A in which a surface profile is described by means of a sine curve. The curve can be described with a wavelength of λ=32 μm and with an amplitude (=Ra value of 3.13 λ/2.50 μm). The defined profile function applies in accordance with equation 1 for the variation in the parameters λ and profile height:

$$z = A_R(x) = \left(\sin\frac{2\pi}{\lambda}x\right)P \quad (7)$$

wherein x is the independent variable, λ is the wavelength and P is the profile height. For the defined profile function in FIG. 2A the equation is:

$$z = A_R(x) = \left(\sin\frac{2\pi}{32}x\right)50 \quad (7a)$$

In that way it is possible to represent all desired surface profiles by way of the basic equations 1-4.

The generalisation of that principle is shown in FIGS. 2B-D with the associated trigonometric basic functions, where it is shown that, besides a sinusoidal profile, it is also possible to produce for example a rectangular profile, a triangular profile and a sawtooth profile. All profiles which can be described with trigonometric functions or series can be produced by means of the method according to the invention. With that mathematical tool it is also possible to draft the parameters sought with Ra values in the range of 1-80 μm and $r_m$ values in the range of 2-50 in a CAD system and determine them for manufacture. Thus such surface structures can be produced into the micrometer range by means of selective electron beam melting (SEBM), selective laser melting or selective laser-assisted manufacture.

FIG. 3 shows that the surface roughness can be described on a surface with two sinusoidal profiles (coordinates: X/Z and YZ). It is further shown how a surface with solid-quadratic profiles can be constructed by means of rectangular functions. FIG. 3A shows a unit cell with a wavelength of λ/2=32 μm, that is to say every 32 μm (wave peak) there is a rectangular profile which in the X- and Y-coordinate involves the same spacing of $\lambda/2=32$ μm (wave trough). The amplitude (Z-axis) for both sinusoidal functions is the identical value of 80 μm ($5\lambda/4$), which corresponds to the Ra value. The entire surface can be divided into unit cells ($3\lambda \times 3\lambda$) of a size of 192×192 μm. A unit cell here has 9 profiles (FIG. 3A). It is also possible to combine a plurality of wavelengths, for example in the X-direction $\lambda/2=32$ and in the Y-direction $\lambda 2=32$ and 16 μm alternately (FIG. 3b). In that way rectangular profiles can now be placed in the same unit cell (192×192 μm) (FIG. 3B). In the case of the rectangular profiles the surfaces can be calculated as follows:

$$F_{profile}=2(xy+xz+yz)-(xy) \quad (3)$$

wherein x, y and z are the specified coordinates and the base area (xy) on which the profile stands has to be subtracted. For areas shown in FIGS. 3A and B and calculated in Table 2 (wave crests) the following then applies:

$$F_{Profile}=2[(\lambda/2)(\lambda/2)+(\lambda 2)(5\lambda/4)+(\lambda/2)(5\lambda/4)]-[(\lambda/2)(\lambda/2)] \quad (4)$$

It is however then necessary to calculate the free areas including the wave troughs.

$$F_{Bottom\ area}=3(\lambda_Y/2 \times L_{EZ})+9 \times (\lambda_X/2)^2 \quad (5)$$

(with the same spacings) or $$F_{Bottom\ area}=3(\lambda_Y/2 \times L_{EX})+12(\lambda_{x1} \times \lambda_{x2}) \quad (6)$$

(with different spacings)
wherein $L_{EZ}$ represents the length of the unit square. Further surface-relevant patterns and profiles which were not taken into consideration in terms of calculation are shown in FIGS. 3C and 3D.

As the calculations in Table 2 show it is possible in that way to very easily construct surfaces with Ra values and $r_m$ values. Thus for the surface A ($\lambda/2=32$ μm) in Table 2 (see also FIG. 3A) that gives a $r_m$ value of 6.0 with a Ra value of 80 μm. If now the Ra value is reduced to 35 μm then the $r_m$ value falls to 3.2 (surface B). If the wavelength is reduced to $\lambda/2=8$ μm with a Ra value of 80 μm then that actually gives a surface having a $r_m$ value=22.6 (surface E). If now the Ra value is reduced to 35 μm that gives a $r_m$ value=11.3, which is also still considerable (surface F).

When using a plurality of different wavelengths substantially higher surface values (surfaces G and H) can be obtained (see FIG. 1B, 12 profiles/unit cell). An attractive possible way of increasing the surface size would be the use of is hollow cylinders or stellate profiles (see FIG. 3D). To sum up Table 2 clearly shows that with the trigonometric approach and parameters in the μm range it is possible to reach Ra values in the range of 2-80 μm and $r_m$ values in the range of $r_m$=3.2-22.6 μm.

Thus, using the available technologies like selective electron beam melting (SEBM), selective laser melting or laser-assisted manufacture (Lasergravur, rapid manufacturing) it is thus possible to produce the surfaces of all biomaterial solid bodies in that way by removal or building up from powders. In that respect a microstructure is possible even at a resolution below 10 μm. The invention shows that computer-controlled production of such implant surfaces is possible.

Advantages of the method according to the invention are thus:
better compatibility due to homogeneity of the surface
large surface areas by way of area increases of 20-40 times
increase in surface capacity for proteins and pharmaceuticals by 20-40 times
increase in ultrahydrophilia
avoidance of infections
pharmaceuticals reservoir in hollow cylinder profiles
computer-aided manufacture (laser and electron beam technology)

According to the invention it is possible to describe all surface structures as trigonometric functions which consequently can be directly represented and simulated as 3D vector graphics in AutoCAD. There are many different variation options in regard to the configuration of the surface according to the invention and the production of unitarially-structured, regular and highly complex surfaces is mathematically pre-defined and can be applied to any surface of any component.

Figure 8:
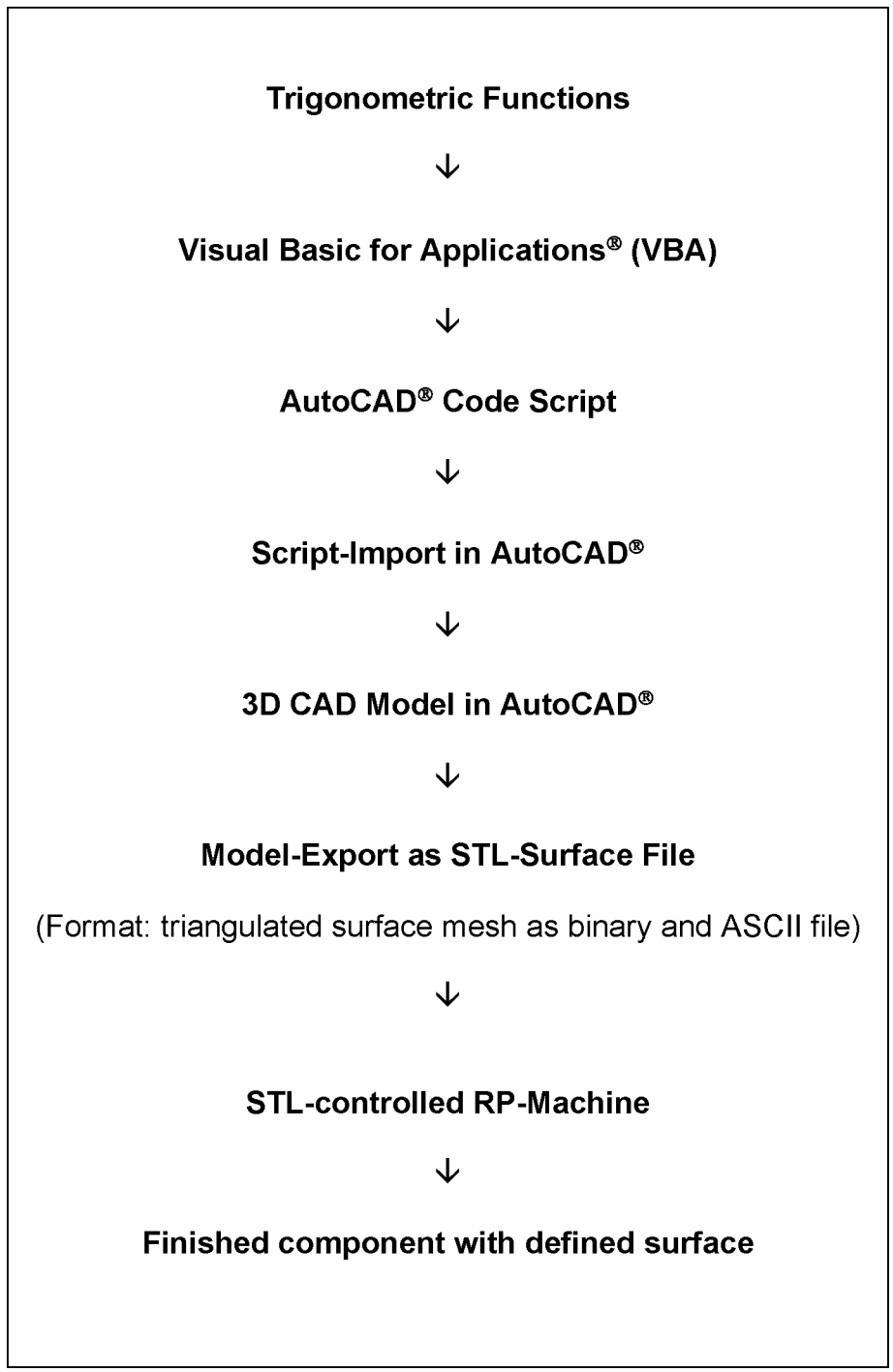
FIG. 8 shows a diagram for conversion of data from a trigonometric function.

Conversion of the data from the trigonometric function for example for a rapid prototyping method and an RP apparatus is diagrammatically shown in FIG. 8.

In a further step peptides like bone growth factors can be immobilised on the microstructures according to the invention optionally superimposed with second microstructures and/or nanostructures, covalently or by means of physiorptive or chemisorptive bonding, presumably on the basis of hydrophilic interactions on the implant material. Adsorptive bonding is also possible after a covalent modification of the surface with amino propyl triethoxy silane (APS) (Table 1). That makes it is possible to form a chemotactically acting and/or biologically active implant surface, with covalent bonding a so-called juxtacrine, leading to accumulation, proliferation and differentiation of bone cells. It is possible in that way to provide so-called biologically active implants which with molecules liberated from the surface, even at a distance of 500 to 1000 μm, exhibit a chemotactic action on cells, in the case of BMPs on osteoblasts.

Preferably adequate loading of the hydrophilised metal surface is achieved by the peptides being applied in a physiological buffer solution in a concentration which is sufficient to achieve a loading of more than 200 ng/cm$^2$, preferably more than 500 ng/cm$^2$ and more preferably more than 1000 ng/cm$^2$ of the peptide on the oxide surface of the metal implant.

In general that loading is achieved with a physiological buffer solution of peptides in a concentration of more than 1 μg/ml, preferably more than 200 μg/ml buffer solution.

According to the invention the peptides are biomolecules which are advantageous for biocompatibility of the implant insofar as they counteract possible rejection of the implant and/or promote ingrowth of the implant.

As mentioned above preferably proteins from the class of TGF proteins, in particular bone growth-promoting proteins from the class of bone growth factors "Bone Morphogenic Proteins" or the class of vascular growth factors like VEGF or angiotropin or also ubiquitin can be used as peptides. The expression "Transforming Growth Factor" (TGF) is used to denote in particular the group (sub-group) of the (i) "Transforming Growth Factors beta" (TGF-β) and the group (sub-group) of the (ii) Bone Morphogenetic Proteins (BMP). The latter are osteo-inductive proteins which simulate bone augmentation and bone healing insofar as they cause proliferation and differentiation of precursor cells to give osteoblasts. In addition they promote the formation of alkali phosphatases, hormone receptors, bone-specific substances like collagen type 1, osteocalcin, osteopontin, osteonectin, Bone Sialoprotein (BSP) and finally mineralisation.

Advantageously for immobilisation purposes it is possible to use a protein of that class alone, in combination with further members of that class or also together with biomolecules like proteins of other classes or low-molecular hormones or also antibiotics to improve immune defence. In that respect those further molecules can also be immobilised on the surface by way of bonds which can be cleaved in the physiological medium.

The invention is described in greater detail by means of the accompanying Figures in which:

FIG. 1 shows REM images of typically wide-spread and successful rough surfaces in dentistry and orthopaedics with A and B SLA surface (sand-blasted acid etched); C and D TPS surface (titanium plasma spray method) and insert FIG. 1C: transfer fracture edge of the TPS surface. The arrow points to the fusion gap between the TPS layer of pure titanium and the base material of titanium alloy (Ti-6Al-4V);

FIG. 2 shows basic shapes of surface protrusions (profiles) as a side view. In this case options for the tip of the profile are round, flat and pointed with $\lambda=32$ µm; $z=50$ µm.

The trigonometric equations describing the profiles are specified under the Figures. All possible forms of the roughness can be described by way of such Fourier series.

Figure 4:
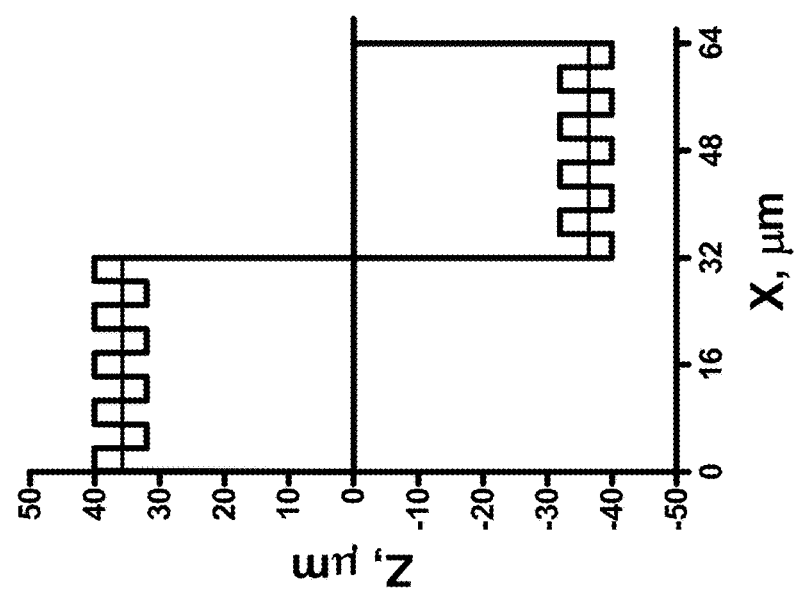
FIG. 4 shows a combination of a first microroughness with a second microroughness.

Associated 3D basic shapes are: A. hyperboloid; B. cuboid; C. pyramids; D. asymmetric pyramids;

FIG. 3 shows unit cells with the respective associated rectangular functions and some profiles (A & B) and arrangement patterns (C) as a cross-sectional view with:
A. unit cell 192 µm×192 µm with 9 profiles ($\lambda x$ and $\lambda y=64$ µm, $z=Ra=80$ µm) (see Table 2, surface A)
B. unit cell 192 µm×192 µm with 12 profiles ($\lambda x$ 64 µm and $\lambda y=32$ µm, $z=Ra=80$ µm); (see Table 2, surface G)
C. arrangement patterns for profiles
D. profiles with different surface area values
3D basic form A-C: cuboid;

FIG. 4 shows a combination of a first microroughness ($\lambda=64$ µm) with a second microroughness ($\lambda=7.1$ µm). The surface area of the macroroughness is increased by the factor of 2.25 (1.5×1.5) by the illustrated second micro roughness.

Figure 6:
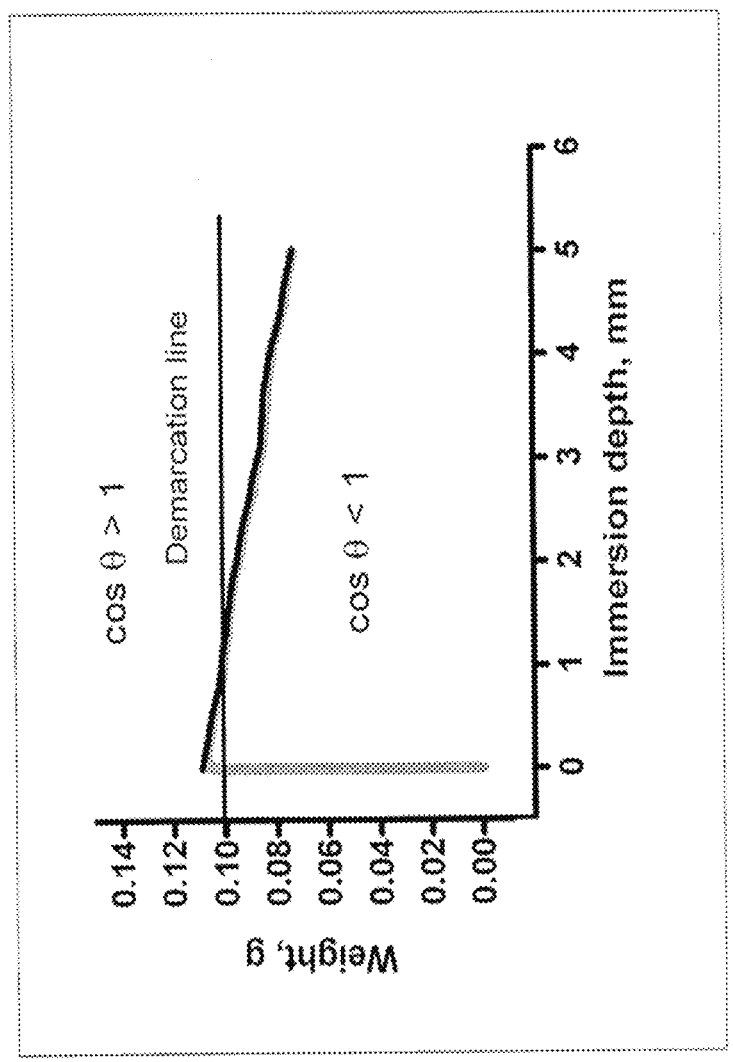
FIG. 6 shows determination of a dynamic contact angle on a surface after chemically "switching over" from a superhydrophobic to a hyperhydrophobic condition.
Figure 7:
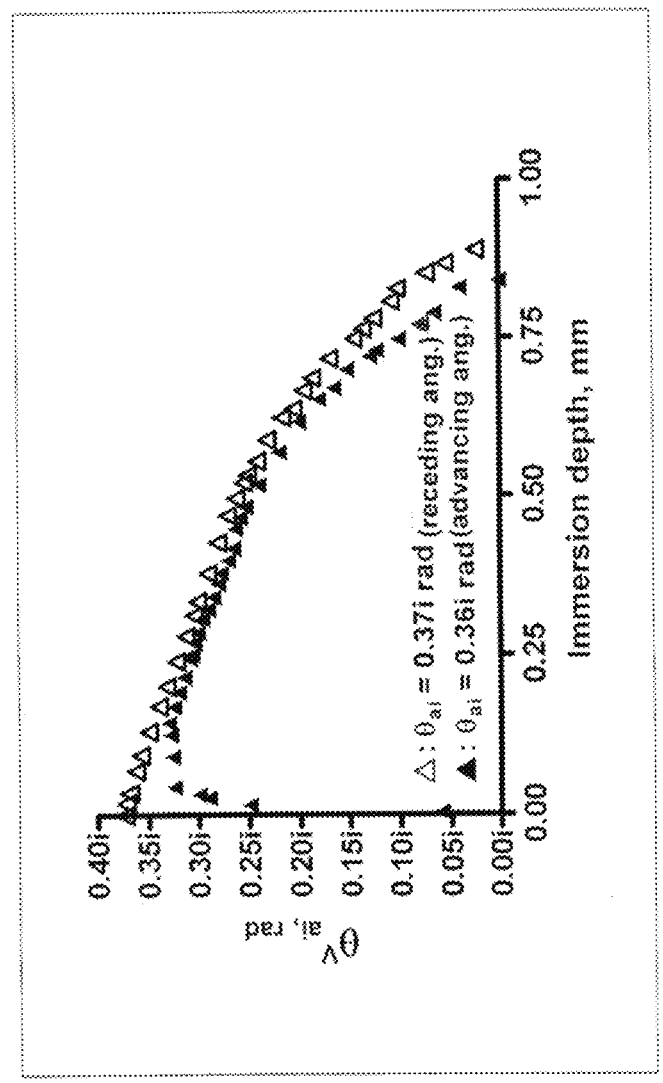
FIG. 7 shows an illustration of the Wilhelmy functions in an undefined region of FIG. 6 as imaginary contact angles in dependence on a depth of immersion.

FIG. 5 shows determination of the static (A) and dynamic (B) contact angle on a superhydrophobic unmodified TPS surface with ultrapure water;

FIG. 6 shows determination of the dynamic contact angle on a surface after chemically "switching over" from the superhydrophobic to the hyperhydrophobic condition;

FIG. 7 shows an illustration of the Wilhelmy functions in the undefined region of FIG. 6 as imaginary contact angles in dependence on the depth of immersion.

Without modification of the above-mentioned microstructure the microstructured surface was further nanostructured in a wet-chemical process and reacted with amino propyl triethoxy silane for the adsorption of BMP-2. For calculation of the monolayer coverage with BMP-2 a footprint of the BMP-2 of 20 $am^2$ (1 µg BMP-2 ~4.6 $cm^2$) was used for a monomolecular coverage of the surface. Under the given conditions the $r_m$ value determined with BMP-2 is well in conformity with the LSM-determined $r_m$ values. The adsorption values obtained are set out in Table 1.

TABLE 1

| Surface | Ra µm | $r_M$ (A'/A) LSM | BMP-2 adsorption (APS-surface) ng/cm$^2$ | | $r'/_M$ (A'/A) BMP-2 |
|---|---|---|---|---|---|
| | | | pro geometr. area (A) | pro actual area (A') | |
| SLA | ~2-3 | 2.5 | 394 ± 66 (6) | 157 ± 27 (6) | 1.8 |
| TPS | 30.0 ± 4.4 (4) | 20 | 5221 ± 293 (6) | 261 ± 15 (6) | 23.9 |

Data Format: ξ±S.D.

According to the invention the surface microstructures can be produced as desired using the trigonometric functions. For that purpose the roughness parameters can be used for a rectangular profile having a profile height of 35 and 80 µm with the values as shown in Table 2.

TABLE 2

| Surface | $\lambda_x$ µm | $\lambda_y$ µm | X $\lambda/2$ µm | Y $\lambda/2$ µm | $F_{Profile}$ µm$^2$ | Profile/ IC | Ra µm | Ry | $r_m$ |
|---|---|---|---|---|---|---|---|---|---|
| A | 64 | 64 | 32 | 32 | 21504 | 9 | 80 | 160 | 6.0 |
| B | 64 | 64 | 32 | 32 | 9 984 | 9 | 35 | 70 | 3.0 |
| C | 32 | 32 | 16 | 16 | 10 496 | 36 | 80 | 160 | 11.6 |
| D | 32 | 32 | 16 | 16 | 4 266 | 36 | 35 | 70 | 6.9 |
| E | 16 | 16 | 8 | 8 | 5 248 | 144 | 80 | 160 | 22.6 |
| F | 16 | 16 | 8 | 8 | 2 304 | 144 | 35 | 70 | 10.3 |
| | | | | $\lambda/2 + \lambda/4$ | | | | | |
| G | 64 | 32 | 32 | 32 + 16 | 21 504 | 12 | 80 | 160 | 7.8 |
| H | 16 | 8 | 8 | 8 + 4 | 2 304 | 192 | 35 | 70 | 13.6 |

The surfaces A and G are shown in FIGS. 3A and 3B. The area of the individual cell (IC) is 36 864 µm$^2$.

Thus, by means of the method according to the invention, it is possible to provide substrates like implants with defined surface structures which are hyperhydrophilic directly after laser-technology production. If the surface is not sufficiently hyperhydrophilic it can be further hyperhydrophilised by means of a chemical hydrophilisation method. Thus these surface structures which can also bear implants lead to particular wetting properties which according to the invention are identified as hyperhydrophilic surfaces. Such chemical hydrophilisation methods include wet-chemical methods like acid etchings and also structured surfaces functionalised by covalent or non-covalent bonding of highly hydrophilic molecules like polyethyene glycol (PEG), poly(2,3-dihydroxypropyl methacrylate) (PDHMA) or poly[2-(methacryloyloxy) ethyl phosphorylcholine] (PMPC), wherein PDHMA and PMPC have a zwitterionic structure. Covalent coupling can be effected for example by way of suitable triethoxy silane derivatives of PEG, PDHMA and PMPC.

As is known in the state of the art, in the present application to characterise wettability hydrophilic surfaces with dynamic contact angles of a value of $0<\theta<10°$ are referred to as ultrahydrophilic while surface with the determinable contact angles according to the invention in the form of imaginary contact angles of a value of $\theta<0i$ to $1.4i$ rad are referred to as hyperhydrophilic.

Usually measurement of the hydrophilicity properties of a surface is effected on the basis of determining the contact angle. Introduction of the contact angle $\theta$ by Thomas Young more than 200 years ago basically opened the way in that respect to understanding wettability by introduction of the Young equation:

$$\gamma_{sv} = \gamma_{sl} + \gamma_{lv} \cos \theta_o \qquad (7)$$

wherein $\gamma_{sv}$, $\gamma_{sl}$ and $\gamma_{lv}$ represent the surface tensions of the phase limits which are in contact of liquid (l), solid body (s) and vapour/gas phase (v), with $\theta_0$ as the equilibrium contact angle for example of a sitting drop. The Young equation which applies to a completely smooth surface is not easy to solve as generally only $\gamma_{lv}$, and $\theta_0$ can be measured.

It is to be noted that the Young equation applies for contact angles applies for ideal, smooth, impermeable surfaces in thermodynamic equilibrium. Contact angles on real rough surfaces in contrast are referred to with the attribute of "apparent" to distinguish them from the Young contact angle on an ideal surface.

Starting therefrom Ludwig Wilhelmy (*Ann. Phys.*, 119, 177-217) found about 60 years later the Wilhelmy balance in which he linked tensiometry to contact angle measurements. In the case of force measurements by means of the Wilhelmy balance the sample is immersed in and removed from ultrapure water, with measurement of the force. The contact angle is then calculated from the force of immersing and removing the sample in accordance with the known Wilhelmy equation:

$$F = P\gamma \cos\theta - V g\rho [N] \quad (8)$$

wherein F represents the measured nett force and in the first term on the right-hand side of the equation P is the perimeter of the sample, γ the surface tension of the water and θ the dynamic contact angle (advancing angle $\theta_V$ or receding angle $\theta_R$). In the second term V denotes the volume of the displaced liquid, g denotes gravity and ρ denotes the density of the liquid. The second term which specifies the buoyancy of the sample in the liquid can be eliminated by extrapolation to the depth of immersion zero and leads to the simplified form of the Wilhelmy equation:

$$\cos\theta = F/(P \times \gamma) \quad (9)$$

If P is equated to the unit of 1 cm (for example plates of 10×5×1 mm) that gives the constant $1/(P\cdot\gamma) = K_\theta = 1.39 \cdot 10^3$ $N^{-1}$ and thus the equation:

$$\cos\theta = K_\theta \cdot F \quad (9a)$$

If contact angles are calculated in accordance with Equation 9 without extrapolation to zero they are referred to as "virtual" contact angles. The use of virtual contact angles is shown hereinafter in FIG. 7.

Considered practically the validity of Equation 9 for a completely smooth surface is limited by two prohibited contact angles: (i) θ≯119° and (ii) θ≮0°. For the first case on the hydrophobic side it is known from the state of the art that contact angles for physical reasons cannot exceed the value θ=110° C. In the second case (θ≮0°) on the hydrophilic side the contact angle cannot be less than zero for the mathematical reason that cos θ>1 is not defined. It was now found on the part of the inventor that this latter barrier in accordance with classic mathematical understanding can be overcome if the contact angles are expanded into the imaginary numerical range ai and thus the surface properties of the implants can be assessed.

For the measurement operations, the inventor used metal plates comprising a titanium alloy coated with pure titanium (Ti-6Al-4V) (so called titanium plasma spray method TPS) with a roughness of Ra=30 μm and a microscopic roughness of $r_m$=20. Dynamic contact angles $\theta_V$ (advancing angle) and $\theta_R$ (receding angle) were determined with ultrapure water using the Wilhelmy method (tensiometer DCAT 11, Dataphysics, Filderstadt, Germany). Immersion and removal speeds were 1 mm/min (17 μm/s) so that the measured contact angles are independent of the dip speed. The apparent static contact angles $\theta_S$' (sitting drop method; 3-5 μl of ultrapure water) were graphically evaluated. The imaginary contact angles were then calculated by the inventor from the measured force values.

The established "extreme hydrophilia (θ>0i) ("hyperhydrophilia")—here in the absence of hysteresis on a microrough surface" after a wet-chemical treatment (acid etching)—was referred to by the inventor here by the term "inverse Lotus effect". That term is also used in the description of hyperhydrophilic surfaces which occurred by way of so-called "chemical switching" from a surface exhibiting the "Lotus effect". Thus a hyperhydrophobic surface (FIG. 5) is "switched over" into a hyperhydrophilic surface by treatment with chromo-sulphuric acid, wherein the latter in accordance with previous analytical methods has an extreme spreading of water ($\theta_S^{H_2O}=0°$) and dynamic contact angles of $\theta_V/\theta_R=0°/0°$) (FIG. 6). As n-hexane and mineral oil spread on those surfaces ($\theta_S^{H_2O}/\theta_S^{Oil}/\theta_S^{n-Hexane} \sim 0°/0°/0°$), they are also referred to as superamphiphilic. The "reverse transformation" from the hyperhydrophilic condition into the hydrophobic condition occurs spontaneous slowly in air if the surface is not conserved.

The invention is also directed to a method in which the treatment to produce a nanostructure includes the step of a wet-chemical treatment of the microstructured surface, wherein a hydrophobic or weakly hydrophilic surface is converted into an ultrahydrophilic or hyperhydrophilic surface, wherein at least one of the two dynamic contact angles ($\theta_V$ and $\theta_R$) is in the range $$\frac{\Delta F}{P \cdot \gamma} = 0.980 \text{ to } 2.15$$

and preferably in the hyperhydrophilic range $$\frac{\Delta F}{P \cdot \gamma} > 1.0 \text{ to } 1.0619 \ (\theta_a^i > 0° - 0.35i \text{ rad}).$$

The observations on the part of the inventor relating to the sequential occurrence of two different Lotus effects on one and the same surface after "chemical switching" indicates that there is a link between those two effects, which however is still unclear. In the hydrophobic case the influence of roughness on the dynamic contact angle ($\theta_V'/\theta_R'$=98.8°/36.7°) by way of an increase to $\theta_S^{H_2O}\sim145°$ (static method) by heterogeneous wetting is to be clearly seen. On the hydrophilic side however there is lacking a similar effect in respect of surface roughness on a contact angle of zero. The measurements by the inventor showed that all contact angles which lay in the region of cos θ>1 were outputted as contact angles of the value zero. An evaluation according to the invention of the raw data of FIG. 6 now shows that 17% of the measurement points in FIG. 6 give undefined contact angles with cos θ>1. That observation is illustrated in the profile in FIG. 6 by a line of demarcation separating the defined from the undefined region. The inventor now found a way of bringing the data of the Wilhelmy measurements from the undefined condition into a defined condition.

TABLE 3

| Validity range | Continuous range of the imaginary and real contact angles | | |
|---|---|---|---|
| | arccos ($K_\theta \cdot F$), rad | $\theta_{ai}^a$, degrees | $K_\theta \cdot F$ |
| | 1.40i | 80.21i | 2.1509 |
| | 1.23i | 70.47i | 1.8568 |
| | 1.05i | 60.16i | 1.6038 |
| | 0.87i | 49.85i | 1.4029 |
| | 0.71i | 40.68i | 1.2628 |
| | 0.53i | 30.37i | 1.1438 |
| Central region of the inverse Lotus effect | 0.35i | 20.05i | 1.0619 |
| | 0.18i | 10.31i | 1.0162 |
| | 0.04i | 2.29i | 1.0008 |
| | 0.00 | 0i | +1.0 |
| Hyperhydrophilia | | ⇑ | |

TABLE 3-continued

| Validity range | Continuous range of the imaginary and real contact angles | | $K_\theta \cdot F$ |
|---|---|---|---|
| | arccos ($K_\theta \cdot F$), rad | $\theta_{ai}{}^a$, degrees | |
| Ultrahydrophilia | cos θ ≥ 1)<br>cos θ ≤ 1)<br>⇓ | | |
| | 0.00 | 0 | +1.0 |
| | 0.04 | 2.29 | 0.9992 |
| | 0.18 | 10.31 | 0.9838 |
| | 0.35 | 20.05 | 0.9397 |
| | 0.53 | 30.37 | 0.8628 |
| | 0.71 | 40.68 | 0.7584 |
| | 0.87 | 49.85 | 0.6448 |
| | 1.05 | 60.16 | 0.4976 |
| | 1.23 | 70.47 | 0.3342 |
| | 1.40 | 80.21 | 0.1699 |
| | 1.57 | 90.00 | 0 |
| | 3.14 | 180.00 | −1.0 |
| | $K_\theta$ | | |

(i) Table 3 shows classic and novel imaginary contact angles $\theta_{ai}{}^a$ in radians and degrees, which were calculated in accordance with the ($K_\theta \cdot F$) values. In that respect imaginary and real contact angle series behave like mirror images in relation to zero. The "inverse Lotus effect" extends from 0.18 rad (~10°) in the real to 1.4i rad (~80°) in the imaginary range of numbers preferably from 0.18 rad to 0.35 rad (~20°). In that respect one of the dynamic contact angles (for example $\theta_A$) can be classic and the second (for example $\theta_{ai,R}$) can be imaginary, which is referred to as a hybrid contact angle pair. On the other hand both dynamic contact angles ($\theta_{ai,V}/\theta_{ai,R}$) can also be imaginary (pure imaginary contact angle pair). Multiplication of the radian value by 180/π leads to the contact angle in degrees: 57.3×0.4i [rad]=22.9i°. For $K_\theta \cdot F$>1.0 there is an imaginary contact angle of >0.0i rad and >0.0i degrees respectively. That is defined as the lower limit for imaginary contact angles.

These findings give the expansion of the Wilhelmy equation into the imaginary range of numbers:

$$\cos \theta_{ai}{}^a = F/(P \times \gamma) \quad (10)$$

The general expression $\theta_{ai}{}^a$ denotes all contact angles in the real range (superscript a) for the boundary condition ($K_\theta \cdot F$)<1 and all contact angles in the imaginary range (subscript ai) for the boundary condition $K_\theta \cdot F$>1 (see Table 3).

Now, by means of equation 10, it is possible to specify defined contact angles for all force measurements in the range ($K_\theta \cdot F$)=1.0 to +2.15 starting from the real number system of cos(180°) to the imaginary system of cos (80i°) (see Table 3). Larger imaginary contact angles up to 180i° are conceivable on rough surfaces according to the inventor's assumptions.

The use of imaginary contact angles for determining a highly wettable TPS surface is shown in FIG. 7. 45 representative values of the raw data above the line of demarcation at 0.102 g in FIG. 6 were selected and their force values ($K_\theta \cdot F$; in the range 1.00 to 1.07) were converted into virtual imaginary contact angles (θai) and plotted as a function of the depth of immersion. Extrapolation of the linear component of the curves to the position zero of the depth of immersion gave the apparent imaginary advancing and receding angles ($\theta_{ai,V}/\theta_{ai,R}$)=0.36i°/0.371°). The imaginary contact angles ascertained in that way are a complex function of the four wetting parameters cohesion, adhesion, spread and immersion. They contain the items of information in respect of those wetting parameters including water absorption and are therefore characteristic of wetting of the illustrated rough surface.

Thus, on the basis of the inventor's realisations, it is possible to determine the properties of such hydrophilic surfaces, for which hitherto such determinations were not possible as in the case of hyperhydrophilic surfaces, and to be able to assess their suitability for subsequent treatments including coating operations.

Thus the invention is also directed to a method for determining the wetting properties of the surface of a substrate, which includes the steps:
a. carrying out a Wilhelmy/force measurement for ascertaining ($K_\theta \cdot F$);
b. calculating the apparent contact angles $\theta_V$ and $\theta_R$ on the basis of the result of step a), wherein said calculation
  i. is effected for the situation where ($K_\theta \cdot F$)≤1 in accordance with arccos ($K_\theta \cdot F$)=real contact angles; and
  ii. is effected for the situation where ($K_\theta \cdot F$)>1 in accordance with arccos ($K_\theta \cdot F$)=imaginary contact angles; and
c. determining the wetting properties of the substrate on the basis of the contact angles $\theta_V$ and $\theta_R$ calculated in step b).

The method according to the invention thus makes it possible to specifically distinguish hyperhydrophilic surfaces from the hydrophilic surfaces and sort out such materials. Thus the wetting properties can be classified from hydrophobic by way of hydrophilic and superhydrophilic to ultrahydrophilic with the contact angles linked thereto.

The invention also concerns an apparatus for carrying out the above-mentioned method which includes a measuring unit, an evaluation unit and an output unit, wherein the measuring unit is adapted for force measurement of the Wilhelmy/force measurement, the evaluation unit is adapted to convert the measurement values obtained by the measuring unit by means an algorithm into an imaginary advancing angle ($\theta_V$) and receding angle ($\theta_R$) and the output unit is adapted to further process the contact angle obtained by the evaluation unit. In that respect further processing can include contact angle display in degrees or radians.

Thus it is possible on the basis of the inventor's realisations to determine the properties of such hydrophilic surfaces, for which hitherto such determination operations were not possible as in the case of hyperhydrophilic surfaces and to be able to assess their suitability for subsequent treatments including coating operations.

The invention claimed is:
1. An implant comprising:
an implant having a first microstructured hyperhydrophilic surface with protrusions and depressions, wherein the spacing between the protrusions as a statistical mean is in a range of 1 to 100 μm and a profile height of the protrusions and depressions as a statistical mean is in a range of 1 to 80 μm,
wherein the implant has a microscopic roughness factor ($r_M$) in a range between 2 and 50, and
wherein at least one of two dynamic contact angles $\theta_V$ and $\theta_R$ of the hyperhydrophilic surface is in a hyperhydrophilic range with 1.0<ΔF/(P·γ)≤2.15,
wherein $\theta_V$ stands for advancing angle, $\theta_R$ stands for receding angle, ΔF stands for a difference between measured net forces, γ stands for surface tension of water, and P stands for perimeter of the sample.

2. An implant according to claim 1 wherein the first microstructured hyperhydrophilic surface is superimposed by a second microstructure with second protrusions and depressions, wherein the spacing between the second protrusions as a statistical mean is in the range of 0.1 to 10 µm and the height of the second protrusions and depressions as a statistical mean is in the range of 0.1 to 10 µm.

3. An implant according to claim 1 wherein the first microstructured hyperhydrophilic surface is microstructured irregularly or at least in partial regions regularly.

4. An implant according to claim 1, wherein the first microstructured hyperhydrophilic surface is superimposed with a nanostructure.

5. An implant according to claim 4, wherein the nanostructure is produced by a wet-chemical procedure by chromo-sulphuric acid etching.

6. An implant according to claim 1, wherein at least one of two dynamic contact angles $\theta_V$ and $\theta_R$ is in a hyperhydrophilic range with $1.0<\Delta F/(P\cdot\gamma)\leq 1.0619$.

7. An implant according to claim 1, wherein the implant comprises a titanium/aluminum/vanadium alloy.

8. An implant according to claim 1, wherein the implant comprises chromium nickel steel.

9. An implant according to claim 1, wherein the implant comprises a metal or metal alloy composite material with a ceramic material.

10. An implant according to claim 9, wherein the ceramic material comprises hydroxylapatite, zirconium oxide, or aluminium oxide.

11. An implant according to claim 1, wherein the implant further comprises a salt-bearing exsiccation layer formed on the first microstructured hyperhydrophilic surface.

\* \* \* \* \*